United States Patent [19]

Hastings

[11] Patent Number: 5,017,372

[45] Date of Patent: May 21, 1991

[54] METHOD OF PRODUCING ANTIBODY-FORTIFIED DRY WHEY

[75] Inventor: Donald H. Hastings, Bismarck, N. Dak.

[73] Assignee: Medicis Corporation, New York, N.Y.

[21] Appl. No.: 259,735

[22] Filed: Oct. 19, 1988

Related U.S. Application Data

[63] Continuation of Ser. No. 851,472, Apr. 14, 1986, abandoned.

[51] Int. Cl.$^5$ ............................................. A61K 39/395
[52] U.S. Cl. .................................... 424/85.8; 424/87; 514/54; 530/387; 530/833
[58] Field of Search ................. 424/87, 85.8; 530/833, 530/387; 514/54

[56] References Cited

U.S. PATENT DOCUMENTS

| | | |
|---|---|---|
| 3,127,318 | 3/1964 | Eversole et al. |
| 3,128,230 | 4/1964 | Heinbach ............................ 424/92 X |
| 3,376,198 | 4/1968 | Petersen et al. .................... 424/85.8 |
| 3,646,193 | 2/1972 | Michaelson et al. |
| 3,896,241 | 7/1975 | Malaspina et al. ............. 530/416 X |
| 4,051,235 | 9/1977 | Plymate ............................ 424/85.8 |
| 4,377,569 | 3/1983 | Plymate ............................ 424/85.8 |
| 4,402,938 | 9/1983 | Collins et al. |
| 4,436,658 | 3/1984 | Peyrouset et al. ............. 530/387 X |
| 4,490,290 | 12/1984 | Gani et al. ..................... 424/85.8 X |
| 4,623,541 | 11/1986 | Elliot et al. ........................ 424/85.8 |
| 4,644,056 | 2/1987 | Kothe et al. ........................ 530/387 |
| 4,816,252 | 3/1989 | Stott et al. ........................ 424/85.8 |
| 4,834,974 | 5/1989 | Stott et al. ........................ 424/85.8 |

OTHER PUBLICATIONS

White et al., Principles of Biochemistry, McGraw-Hill Book Company, pp. 824–825 (1968).

*Primary Examiner*—Howard E. Schain
*Attorney, Agent, or Firm*—Jones, Askew & Lunsford

[57] ABSTRACT

A method of producing a dry whey protein powder fortified with naturally occurring polyclonal antibody IgG to preselected infectious intestinal disease antigens, primarily diarrhea-causing enterotoxigenic *Escherichia coli* bacteria bearing colonization factor antigens (CFA) I or II and heat labile toxins. The product is made by first immunizing a pregnant ungulate, such as a cow, by administration of antigens of the preselected disease. After parturition the milk from the ungulate is collected and maintained in its natural state. The milk is subjected to a standard cheese-making process which produces coagulated casein and whey. The antibody IgG is carried into the whey, which is concentrated and dried. The resulting dried protein powder contains the antibody. The product may be administered orally to living beings, both humans and other animals, to prevent contraction of the preselected disease and to treat bodies exposed to the disease.

20 Claims, No Drawings

METHOD OF PRODUCING ANTIBODY-FORTIFIED DRY WHEY

This application is a continuation of Ser. No. 851,472, filed Apr. 14, 1986, now abandoned.

FIELD OF THE INVENTION

1. Background of the Invention

This invention relates to a method of commercially producing a dried whey product naturally fortified with naturally occurring antibodies to preselected antigens for the prevention and treatment of human diseases. The invention relates to the commercial processing into whey of milk produced in the mammary glands of ungulates that contains high specific antibody effective against a wide range of antigens that cause disease. More particularly, the invention concerns the commercial production of a dried whey protein product from milk in its natural state fortified with naturally occurring antibodies to preselected antigens. Specifically, this invention was developed using a vaccine made from enterotoxigenic *Escherichia coli* (ETEC) bacteria bearing colonization factor antigen I and II (CFA I and CFA II) and heat labile enterotoxins.

The term "milk in its natural state", as used herein, means milk or colostrum in the form in which it comes from the udder of a cow or other ungulates and prior to processing of any kind.

Naturally occurring antibodies refers to antibodies occurring in the milk as a result of the natural metabolic processes of the cow, even through subject to external influences. It does not refer to antibodies added to milk subsequent to milking. The term "antigen" refers to a material antigenic to an ungulate.

2. The Prior Art

In an abandoned patent application, Ser. No. 628,987, filed Nov. 15, 1945, an abstract of which was published in the U.S. Patent Office Gazette on Dec. 5, 1950, the applicant, Holm, suggests that possibility of treating disease by the ingestion of milk fortified with naturally occurring antibodies where said antibodies have been induced by actively immunizing a cow with a preselected antigen. However, Holm failed to secure a significant number of antibodies because he followed the usual immunization procedure of intramuscular and intravenous injections of antigen, hoping that the milk would absorb a significant proportion of these antibodies from the blood of the animal. This type of injection does not yield a therapeutically significant concentration of antibodies in milk in its natural state.

In August, 1951, Porter published his doctoral thesis at the University of Minnesota. (The role of plasma cells in the production of globulin within the mammary glands and time studies on antibody response from experimentally induced inflammation of the udder, abstracted in Biochemical Abstracts, 1953, p. 951, per 10,185), in which he suggested the possibility of manufacturing antibodies in the cow's udder by infusion of antigen into the udder of a lactating cow. This was a revolutionary departure from prior thinking, for although it was known that relatively minor quantities of antibodies could enter the milk from the blood stream and that antigens could exercise their effects via the udder, it was not thought that the udder itself could play a significant manufacturing role in the immunity scheme.

Porter, therefore, suggested the infusion of selected antigens into the cow's udder during the lactation period with the hope of increasing the effective concentration of antibody in milk in its natural state to effective economic levels. However, Porter's proposal, like Holm's procedure, was incapable of accomplishing the desired results.

In addition to the problem of securing an increase in numbers of antibodies in milk in its natural state, there is also the extremely important matter of economic feasibility in relation to procedural requirements. Although it is possible with the methods of Holm and Porter to produce antibody-containing milk, and also possible to employ well known concentration procedures to reach some effective level of therapeutic concentration, this would not be economically feasible for the reason that the high cost of producing such antibodies precludes any widespread use.

The method of antibody production in the cow's udder which will yield milk in its natural state with the required concentration of antibodies, without requiring further concentrating or processing of the milk, was not achieved by either Holm or Porter.

In U.S. Pat. No. 3,376,198, issued on Apr. 2, 1968, the patentees, Petersen and Campbell, disclose procedures and methods to produce high concentrations of any specific antibody in the milk of ungulates (particularly cows, goats, sheep, etc.) against any antigen by introducing such antigen into the udder of the animal during preparturition period, that is, during pregnancy. Subsequent to parturition, declining antibody concentrations can be increased by periodically introducing booster shots of the selected antigen into the udder during the lactating period.

The antigenic substances which were employed by Peterson and Campbell in their invention for the production of antibodies or "protective principles" include bacteria, viruses, proteins, animal tissue, plant tissue, spermatazoa, rickettsia, metazoan parasites, mycotic molds, fungi, pollens, dust, and similar substances which are antigenic to an ungulate.

The antibody or "protective principle" produced in accordance with Peterson and Campbell's invention may be preserved, if desired, in pasteurized milk, condensed milk, dried milk, and in gamma globulin isolated from the milk. Pasteurization has no adverse effects upon the "protective principle".

The milk containing "protective principle" may be freeze-wired or may be condensed under careful temperature control. Dried milk containing the antibody or "protective principle" is preferably prepared from the non-condensed product. However, the condensed milk may be used if at first condensed carefully at low temperature to avoid destroying the "protective principle".

Drying can also be accomplished by the conventional spray or roller drying processes under properly controlled conditions in order to preserve the "protective principle". High temperatures per se are not detrimental to the "protective principle" except when sustained for a period of minutes. Thus, the milk may be dried in a dryer in which temperatures of 300 to 400 degrees F. are achieved, if the milk is at these temperatures only for an instant.

The isolated and separated antibodies or "protective principle" may be administered orally, rectally, parenterally, and topically. The "protective principle" is useful in the immunization and treatment of animals. The "protective principle" may be made to protect chickens and pigs as well as ungulates. The procedures of U.S. Pat. No. 3,376,198 did not achieve an economical method of processing large quantities of antibodies or "protective princple" in whey from cow's milk.

The principal object of the present invention is to produce a dried whey powder from cow's milk with naturally occurring antibodies on a commercial scale so large quantities of antibodies can be produced, concentrated, stored, and marketed worldwide to protect against disease, particularly travelers' diarrhea caused by enterotoxigenic *Escherichia coli* (ETEC) bearing colonization factor antigens I and II (CFA I and CFA II) and heat labile enterotoxins. According to M. M. Levine (Travelers' Diarrhea: Prospects for successful immune prophylaxis. Sand. J. Gastroentrol. 18:121–124, 1983, suppl. 84), this is the bacteria that causes 22–75% of the Travelers' diarrhea cases that occur in 29–57% of the travelers to less-developed countries.

Vaccination of humans with pure CFA pili (free threadlike appendages of the antigen) have not been protective. Although whole cell pili bacteria show more promise, active immunization requires vaccination several weeks before exposure, whereas passive protection according to the present invention gives "within minutes" protection. Investigators are enthusiastic in their hopes for passive gut protection because of recent success in veterinary medical studies.

The preparturient vaccination of cows with the colonization antigen K99 of enterotoxigenic *Escherichia coli* (ETEC) will increase the cow's colostrum titers to an average of 1:450. Titers up to 1:4096 have been reported, whereas non-vaccinated titers are 1:3.4. The high titer milk protects the calf from its endemic ETEC environment. The preparturient vaccination gives "within minutes" protection against ETEC diarrhea, safely, conveniently, and economically via the milk.

Preparturient vaccination of cows with rotavirus produces anti-rotavirus titers of 1:5120 in the first milk. This protects the calf against rotavirus diarrhea.

The successful use of a single dose (10 ml–1:1280) specific monoclonal antibody IgG derived from and used against bovine colonization pili ETEC K99 given orally to the newborn calf will confer protection to the calf from fatal ETEC K99 present in his environment. It has been determined that the calf will develop protective active gut immunity that protects it after the monoclonal immunity is passed.

SUMMARY OF THE PRESENT INVENTION

The invention is directed to a method of producing a dry whey protein powder product fortified with naturally occurring polyclonal antibody IgG to preselected infectious intestinal disease antigens, primarily diarrhea-causing enterotoxigenic *Escherichia coli* bacteria bearing at least one of colonization factor antigens (CFA) I or II and heat labile toxins. The product is made by first immunizing a pregnant ungulate, such as a cow, by administration of antigens, in a non-pathogenic condition, of the preselected disease. After parturition the milk from the ungulate is collected and maintained in its natural state. When sufficient milk has been collected, it is subjected to a standard commercial cheesemaking process which produces coagulated casein, which is processed into cheese, and whey. The antibody IgG is carried into the whey, which is concentrated and dried. There are several classes of immunoglobulins in milk: IgG, $IgG_2$, IgA and IgM. IgG as used herein is inclusive of all of these but primarily IgG and $IgG_2$. The resulting dried protein powder contains the antibody. The product may be administered orally to living beings, both human and other animals, to prevent contraction of the preselected disease and to treat bodies exposed to the disease.

DETAILED DESCRIPTION OF THE PREFERRED EMBODIMENT

According to the present invention, a pregnant ungulate is first immunized against a preselected infectious intestinal disease. Although the cow is the preferred ungulate, goats, sheep and others may be used. Antigens which produce various known infectious diseases are readily available. Vaccines containing the antigens in a non-pathogenic condition are made by methods well known in the art. The pregnant ungulate is immunized by administration of the vaccine subcutaneously or diathially (through the teat) or by a combination of these methods. Vaccination preferably occurs about 6 to 10 weeks prior to parturition. Booster shots desirably are administered at intervals of 1 to 3 weeks. Further booster shots may be given during the lactation period after parturition to maintain the level of antibody production.

After parturition, the milk containing antibodies is collected and maintained in its natural state and transported to a commercial cheese-making plant. Preferably a large number of animals are under treatment at any given time such that their milk may be pooled and subjected to the cheese-making process on a continuing commercial scale. In accord with standard cheese-making processes, the antibody milk is subjected to starter-rennet coagulation of the milk casein, which is processed into cheese.

The antibodies remain with the whey which is concentrated and dried into a powder product for ease of packaging, storage, transport and oral administration to a living subject. The product may be administered prophylactically to one likely to be exposed to an infectious intestinal disease, such as diarrhea, by travel in an under-developed area to ward off the disease. The prophylactic dose can be taken orally several hours after arrival in an endemic—ETEC area. Based on studies on adult human gut denaturation of the immunoglobulin which have been conducted, it has been determined that the immunoglobulins retain their activity.

The whey is preferably initially concentrated by membrane filtration (ultrafiltration) to remove lactose, some of the minerals and water. Additional minerals and water are removed by reverse osmosis to further concentrate the whey. The concentrate may then be spray dried. The resulting whey protein powder has a titer to CFA I between about 1:240 to 1:320 and to CFA II between about 1:960 to 1:1280. This powder may be administered orally in dry powder form in doses of from about 10 to 40 grams. Alternatively, the powder may be mixed with water or other potable beverage liquid and drunk. The powder may also be distributed in tablet or capsule form, or desirably in food form processed in a manner to prevent denaturation of the active globulins. For example, the whey powder may be incorporated into candy bars or granola bars, or the like for ease of administration.

More specifically, the antibodies of the present invention were produced by the following procedures:

(1) Obtained and Verified Bacteria

Strains of ETEC bearing CFA I and CFA II were obtained from the Center for Vaccine Development, University of Maryland, School of Medicine. The ETEC strains were reconfirmed as bearing CFA I and CFA II fimbriae (hairlike components of the antigens) by electron microscopy. The two strains were replated for 18 hours on CFA agar. CFA agar is known to encourage the production of CFA fimbriae and consists of 1% Casamino acids (Difco), 0.15% yeast extracts (Difco), 0.05% $MgSO_4$ and 0.0005% $MnCl_2$ plus 2% agar with the pH adjusted to 7.4.

(2) Stored Bacteria

A few loops of each culture were put into cryovials containing tryptose soy broth containing 15% glycerin and frozen in liquid nitrogen for future use.

(3) Reconfirmed Bacteria

To produce the vaccine to be used to immunize dairy cows the following procedure was used: known strains of ETEC bearing CFA I and CFA II were removed from the nitrogen storage tank, thawed enough to put a loop of each on CFA agar and cultured at 37° C. for 18 hours. CFA I fimbriae was confirmed by hemagglutination of human, chicken, and bovine erythrocytes in the presence of 1% mannose, a hemagglutination property of CFA I-bearing ETEC.

CFA II was confirmed by the agglutination of a culture suspension of CFA II antiserum provided by the Center for Vaccine Development. CFA II can be confirmed by the hemagglutination procedure, if necessary. CFA II is sensitive to 1% mannose and will not hemagglutinate human cells in its presence, but it will hemagglutinate bovine red cells.

(4) Increased Bacterial Population

Ten 100 mm CFA agar plates were inoculated with each strain of reconfirmed CFA I and CFA II bearing *E. coli*. Sterile cotton swabs were used to inoculate the increase plates from the first isolation of CFA plates. After 24 hours of incubation at 37° C. the colonies of the cultures from each strain were harvested by gently scraping with a sterile glass slide. The colony mass was placed into a 500 cc of sterile Phosphate Buffered saline (PBS). CFA I and CFA II reconfirming tests were done on each bacterial suspension.

(5) Made Vaccine

A volume of 2.5 ml of 40% formulin was added to each 500 ml of bacterial suspension to kill the bacteria and to form toxoids from any toxins that may be present. Both strains of ETEC provided by the Center for Vaccine Development were strains that each produce heat-labile toxins (LT) and heat stable toxins (ST). Heat labile toxins are immunogenic, whereas the peptides of heat stable toxins are non-immunogenic unless conjugated to carrier proteins. Primary efforts were directed toward obtaining an immune respondence in the dairy cows to CFA I and CFA II antigens. However, the incorporation of LT toxoids into the immunization vaccine provides an adjuvant effect to the CFA antigens as well as the production of anti-LT immunoglobulins which can neutralize toxins.

Negative CFA I and CFA II control cultures were made by culturing both strains of CFA agar at 1820 C. This killed bacterial suspension was used to absorb anti-*E. coli* immunoglobulins leaving more pure anti-CFA I and CFA II antiglobulins in serums and whey. Fimbriae-bearing *E. coli* do not produce fimbriae at 18° C. incubation temperature.

The formalized bacterial suspension was diluted with formalized saline to give a bacterial concentration of $12 \times 10^8$ (density estimated to be a McFarland 4). 400 cc of this suspension was processed through a continuous flow ultrasonic cell dismembrators to free more anitgenic CFA I and CFA II fimbriae and heat labile toxins, and the pH was adjusted to 6.7. An adjuvant aluminum hydroxide gel was added (5 mg/ml) to 250 cc of each ultrasound-processed bacterial suspension to make the vaccine for systemic immunization. The remaining ultrasounded suspension was used for diathelic immunization.

(6) Immunized Cows by Diathial and Subcutaneous Methods

One adult holstein milk cow, seven months pregnant, was used for the trials. The cow was tested for tuberculosis and brucellosis by standard USDA procedures. Blood serums were saved and frozen for future use. The cow was given a priming dose (50-50 combination of CFA I and CFA II bacteria) of 5 cc of the $Al(OH)_3$ suspension subcutaneously eight weeks before parturition and then boostered at two-wee intervals. The cow was diathially immunized with 10 cc of the 50-50 combination of CFA I and CFA II non-$Al(OH)_3$ suspension infused into each teat canal and massaged up into each quarter of the mammary gland six and three weeks before parturition. After the cow calved, the titers were evaluated.

(7) Collected Colostrum

Upon calving, the first four milkings of colostrum were collected, pooled, frozen and held at $-16°$ C. from one cow. At calving a serum sample from the cow was collected and frozen.

The cow was housed and milked by a cooperating dairyman. However, milk and serum samples were collected at monthly intervals for a period of at least six months to measure titers.

To measure anti-CFA I and CFA II immunoglobulins in the colostrum and milk samples, whey was produced and titer measured according to the following technique.

(8) Produced Whey

The whey used in the agglutination tests was prepared from the milk in the following manner. The frozen samples were thawed slowly at 26° C. One ml of whole milk or colorstrum was added to 8.6 ml of distilled water and placed in a 38° C. water bath. The casein protein was precipitated by the addition of 0.2 ml of 10% acetic acid. The pH was brought down to 4.6 and held in a 38° C. water bath for 15 minutes. The sample was then centrifuged for 15 minutes. The whey fraction was removed and the pH adjusted to 6.4 by use of 1.N solution NaOH. he whey sample was filter sterilized through a 25 mm disposable filter. This technique produced a 1:10 dilution of a clear whey from the milk or colostrum sample.

(9) Measured Amount of Titer

A plate agglutination test was performed by mixing 0.1 ml of whey with 0.1 ml of antigen on a clean glass plate. Antigen was obtained from the formalized cultures (non-$Al(OH)_3$) which was centrifuged and washed six times with PBS to remove the formalin and finally suspended in PBS to a density approximately McFarland 5. Agglutination was observed after 15 minutes of incubation at room temperature using a 6X binocular microscope. Ten fold serial dilutions were made using standard methods to obtain final titers.

Tube agglutination test (Widal) were utilized to determine titers. Serial dilutions of whey were made to which washed *E. coli* antigen (density near McFarland 2) was added. The tube was mixed then incubated at 37° C. for 18 hours and observed for agglutination.

In addition, the non-fimbriae ETEC immunoglobulins were absorbed out in the whey samples by incubating the whey samples with the ETC cell suspension from the 18° C. incubation cultures (1 hour at 37° C.). The centrifuged whey should be more specific for just CFA I and CFA II globulins. Therefore, titer evaluations are more accurate. Elisa test using antibody techniques was also used to determine titers.

(10) Made Dried Whey Protein Concentrate Product

A dried whey protein containing immunoglobulins available for use in clinical studies was prepared from the fresh whey.

Frozen milk from the cow was slowly thawed, pooled, mixed, and brought to 37° C. HCl (1.0N) was added slowly to reduce the pH to 4.6. After one hour of incubation at 37° C., precipitated casein was diced, slowly stirred and removed by sedimentation, filtration, and centrifugation. The pH was adjusted to 6.8 by 1.N NaOH. The resulting colostrum whey was frozen until the final processing and drying without any loss of activity.

If the titers are considered too low, more intense systematic immunization schedules can be carried out before and after parturition to maintain titers.

EXAMPLE 1

Following the described procedure, production of immunoglobulins to human *E. coli* attachment pili was demonstrated by immunization of a prepartuent cow with an *E. coli* bacterin made from a known Enterotoxigenic *E. coli* strain supplied by the National Institute of Health and the Center for Vaccine Development, University of Maryland. Each *E. coli* bearing CFA I (M452Cl) or CFA II (E2437A) pili was clotured to promote the production of pili. The cow as immunized systemically 4 times with both types of pili at 2 week intervals before calving. The colostrum was saved and frozen. The colostrum was thawed and whey was produced. The whey antibody titers were determined at 1:5120 to CFA II and 1:320 to CFA I.

EXAMPLE 2

Another strain of *E. coli* (H10407) bearing CFA I was cultured. A human challenge was performed. The subject, on an empty stomach, took four ounces of water containing 5 grams of Na Bicarbonate. After waiting 10 minutes, he drank a 50 cc solution of the plate washing of *E. coli* (H10407) CFA I bacteria concentrated at $21 \times 10^8$. He waited 30 minutes and then drank 150 cc of colostrum from the immunized cow of Example 1. No diarrhea occurred in the subsequent seven days, thus demonstrating the principle of protection.

EXAMPLE 3

Eight months post-calving milk from the immunized cow used in Example 1 was collected and anti CFA I and CFA II titers were determined. Whey was produced. The whey had a titer of 1:80 against CFA II and 1:10 against CFA I. This demonstrated there were antibodies still present in the milk several months after calving. The whey was freeze dried. The resulting powder, when suspended in 4 parts water had a titer of 1:80 to CFA I and a titer to CFA II over 1:320. This demonstrated the antibodies can be concentrated from whey.

EXAMPLE 4

A challenge was made using another strain of *E. coli* (M452CT) CFA I. A 50 cc solution of *E. coli* plate wash diluted to $21 \times 10^8$ was taken after an overnight fast and a bicarbonate wash. This was followed by drinking a solution of 100 grams of freeze-dried whey powder from Example 3, 30 minutes after ingestion of the bacteria. One soft stool was reported 48 hours after the challenge and then stools returned to normal. The typical watery enterotoxigenic diarrhea was not reported, thus showing antibodies can be utilized from the whey concentrate.

EXAMPLE 5

A herd of 100 dairy cows in all stages of lactation and pregnancy were immunized using the *E. coli* bacterin containing CFA I and CFA II vaccines similar to Example 1. They were vaccinated at three week intervals. Three weeks following the third vaccination, the bulk milk composite of all the 60 milking cows of the group had a whey titer to CFA I of 1:40 and a titer over 1:320 to CFA II. 7600 pounds of milk were processed from this dairy farm at a local cheese plant. 4870 pounds of whey were obtained and concentrated by vacuum evaporation and spray dried. The resulting 205 pounds of powder with 14% protein had a titer of over 1:320 to CFA II and the 1:40 titer to CFA I. This demonstrated a dairy herd can be immunized to produce the specific immunoglobulins which are passed in its milk. This also demonstrated that specific immunoglobulin activity can be maintained to a final dried whey powder by using the commercial cheese making process and commercial whey concentrating processes.

EXAMPLE 6

A challenge study was performed utilizing the dried whey powder obtained from the milk from the immunized dairy herd in Example 5. The human subject took 25 grams of whey powder orally each day for three days. On the third day, three hours after taking 25 grams of the whey powder a bicarbonate prewash was taken on an empty stomach. Ten minutes later a 50 cc solution of Enterotoxigenic *E. coli* bacteria CFA II (M408CT) plate washing concentrated at $21 \times 10^8$ was taken orally. On the following five days after challenge, 25 grams of whey powder were taken each morning. On the third day after challenge two soft stools were reported in a four hour period. Then the stools returned to normal. The challenge was without typical enterotoxigenic diarrhea. This demonstrated the existence of the antibodies in the dried whey powder.

EXAMPLE 7

Utilizing by-product whey from commercial cheese manufacturing, whey proteins can be concentrated by membrane filtration and reverse osmosis, thus increasing the whey protein levels to 50% or more, by the removal of lactose and salts and water. The use of this method of concentrating instead of evaporative vacuum condensation prevents the moderate denaturation of immunoglobulins subjected to the evaporative vacuum technique. The amount of antibodies can be increased up to 5 times. Therefore, they whey protein concentrate can be more practical in dosage while still maintaining the required amount of activity.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A dry whey protein powder fortified with polyclonal antibodies against preselected infectious intestinal disease antigens made according to a method comprising the steps of:
   a. immunizing a pregnant ungulate by administration to the ungulate of the preselected infectious intestinal disease antigens in a non-pathogenic condition;
   b. collecting and maintaining the milk from the ungulate after parturition, the milk containing a higher than normal concentration of antibodies against the preselected infectious intestinal disease antigens because of the immunization step;
   c. producing unfractionated whey fortified with naturally occurring polyclonal antibodies against the preselected infectious intestinal disease antigens from the milk by removing milk casein; and
   d. concentrating and drying the unfractionated whey to produce a whey protein powder fortified with naturally occurring polyclonal antibodies against the preselected infectious intestinal disease antigens.

2. The dry whey protein powder of claim 1, wherein the preselected infectious intestinal disease antigen is derived from a diarrhea-causing enterotoxigenic *Escherichia coli* bacteria bearing at least one of the colonization factor antigens and heat labile toxins.

3. A method of preventing an intestinal disease in a human or animal comprising prophylactically administering to the human or animal an effective oral dose of a dry whey powder fortified with polyclonal antibodies against antigens associated with the intestinal disease made according to a method comprising the steps of:
   a. immunizing a pregnant ungulate by administration to the ungulate the antigens associated with the intestinal disease in a non-pathogenic condition;
   b. collecting and maintaining the milk from the ungulate after parturition, the milk containing a higher than normal concentration of polyclonal antibodies against antigens associated with the intestinal disease because of the immunization step;
   c. producing unfractionated whey fortified with naturally occurring polyclonal antibodies against the intestinal disease antigens from the milk by removing milk casein; and
   d. concentrating and drying the unfractionated whey to produce a whey protein powder fortified with naturally occurring polyclonal antibodies against the intestinal disease antigens.

4. The method of claim 3, wherein the dry whey powder is mixed with a beverage before administration to the human or animal.

5. The method of claim 3, wherein the dry whey powder is incorporated into a food bar.

6. The method claim 3, wherein the preselected infectious intestinal disease antigen is derived from a diarrhea-causing enterotoxigenic *Escherichia coli* bacteria bearing at least one of the colonization factor antigens and heat labile toxins.

7. The method of claim 6, wherein the dry whey powder is admixed with a beverage before administration to the human or animal.

8. The method of claim 6, wherein the dry whey powder is incorporated into a food bar.

9. A method of treating an intestinal disease in a human or animal comprising administering to the human or animal with the intestinal disease an effective oral dose of a dry whey powder fortified with polyclonal antibodies against antigens associated with the intestinal disease made according to a method comprising the steps of:
   a. immunizing a pregnant ungulate by administration to the ungulate the antigens associated with the intestinal disease in a non-pathogenic condition;
   b. collecting and maintaining the milk from the ungulate after parturition, the milk containing a higher than normal concentration of polyclonal antibodies against antigens associated with the intestinal disease because of the immunization step;
   c. producing unfractionated whey fortified with naturally occurring polyclonal antibodies against the intestinal disease antigens from the milk by removing milk casein; and
   d. concentrating and drying the unfractionated whey to produce a whey protein powder fortified with naturally occurring polyclonal antibodies against the intestinal disease antigens.

10. The method of claim 9, wherein the dry whey powder is admixed with a beverage before administration to the human or animal.

11. The method of claim 9, wherein the dry whey powder is incorporated into a food bar.

12. The method of claim 9, wherein the preselected infectious intestinal disease antigen is derived from a diarrhea-causing enterotoxigenic *Escherichia coli* bacteria bearing at least one of the colonization factor antigens and heat labile toxins.

13. The method of claim 12, wherein the dry whey powder is admixed with a beverage before administration to the human or animal.

14. The method of claim 12, wherein the dry whey powder is incorporated into a food bar.

15. The dry whey protein powder of claim 1, wherein the whey is produced by treating the milk with starter-rennet.

16. The dry whey protein powder of claim 1, wherein the whey is produced by acidification of the milk.

17. The dry whey protein powder of claim 3, wherein the whey is produced by treating the milk with starter-rennet.

18. The dry whey protein powder of claim 3, wherein the whey is produced by acidification of the milk.

19. The dry whey protein powder of claim 9, wherein the whey is produced by treating the milk with starter-rennet.

20. The dry whey protein powder of claim 9, wherein the whey is produced by acidification of the milk.

* * * * *